United States Patent
Duplan et al.

(10) Patent No.: US 7,262,332 B2
(45) Date of Patent: Aug. 28, 2007

(54) PROCESS FOR MULTISTAGE CONVERSION OF A CHARGE COMPRISING OLEFINS WITH FOUR, FIVE OR MORE CARBON ATOMS, WITH THE AIM OF PRODUCING PROPYLENE

(75) Inventors: Jean-Luc Duplan, Irigny (FR); Jérôme Bayle, Lyons (FR); Sylvie Lacombe, Saint Genis Laval (FR); Cécile Thomazeau, Rueil Malmaison (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 140 days.

(21) Appl. No.: 10/507,853

(22) PCT Filed: Mar. 6, 2003

(86) PCT No.: PCT/FR03/00728

§ 371 (c)(1),
(2), (4) Date: May 10, 2005

(87) PCT Pub. No.: WO03/078364

PCT Pub. Date: Sep. 25, 2003

(65) Prior Publication Data

US 2005/0222475 A1    Oct. 6, 2005

(30) Foreign Application Priority Data

Mar. 15, 2002  (FR) .................................. 02 03211

(51) Int. Cl.
*C07C 2/00*     (2006.01)
(52) U.S. Cl. ........................ 585/329; 585/324; 585/653

(58) Field of Classification Search ................. 585/324, 585/329, 653
See application file for complete search history.

(56) References Cited

U.S. PATENT DOCUMENTS

| 6,049,017 A * | 4/2000 | Vora et al. .................. 585/324 |
| 6,165,439 A | 12/2000 | Benazzi et al. |
| 6,337,428 B1 | 1/2002 | Benazzi et al. |
| 6,977,321 B1 * | 12/2005 | Dath et al. .................. 585/653 |

FOREIGN PATENT DOCUMENTS

| EP | 0109059 | 5/1984 |
| FR | 2755958 | 5/1998 |
| WO | WO9412452 | 6/1994 |
| WO | WO9929805 | 6/1999 |

* cited by examiner

*Primary Examiner*—Glenn Caldarola
*Assistant Examiner*—Prem C. Singh
(74) *Attorney, Agent, or Firm*—Millen, White, Zelano & Branigan, P.C.

(57) ABSTRACT

The invention relates to a process for production of propylene in particular from a C4 and/or C5 cut from steam cracking and/or catalytic cracking, preferably comprising both butenes and pentenes, said process comprising at least one oligomerization stage, followed by a stage of catalytic cracking of the oligomers formed.

Figure 1:
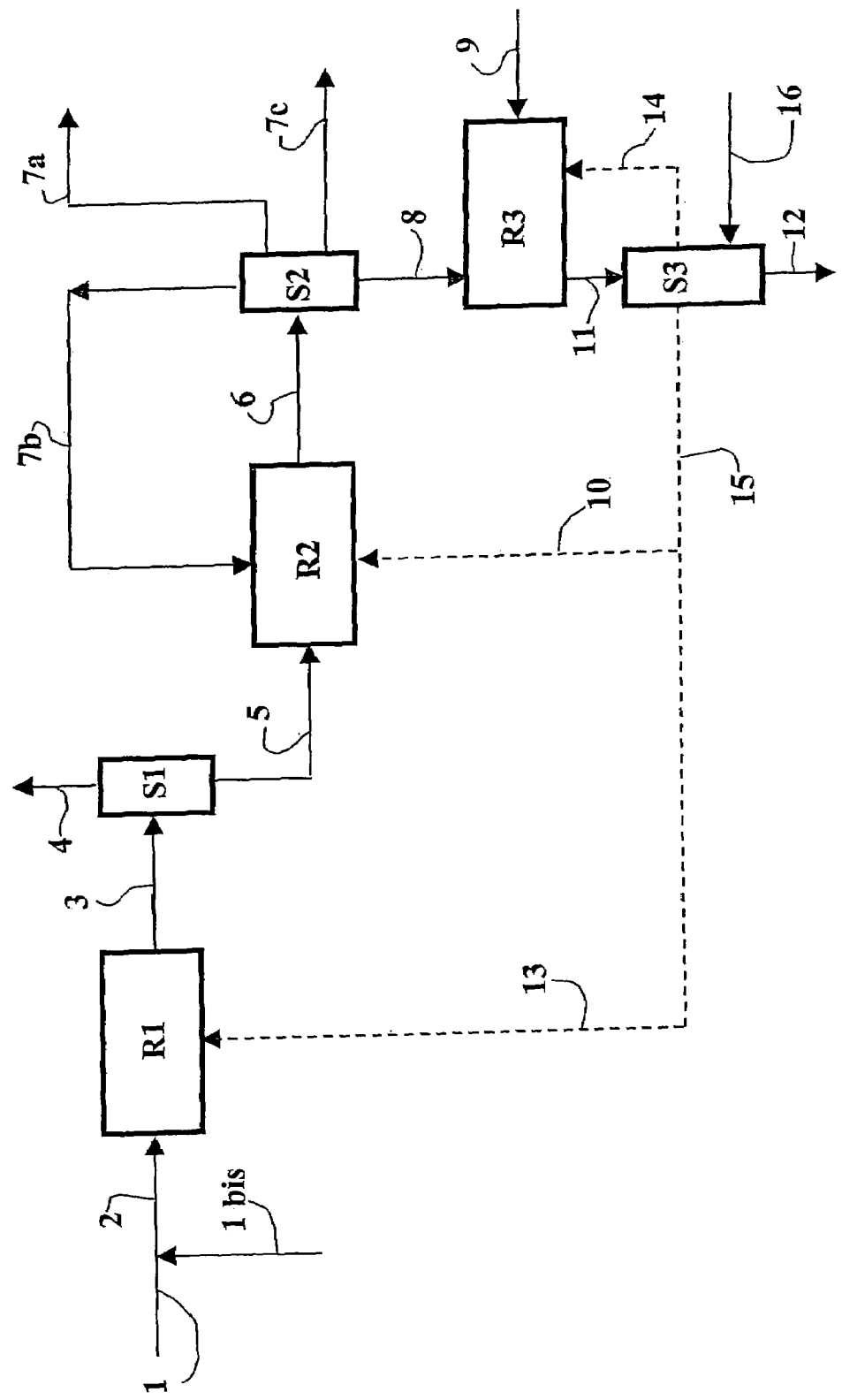

Preliminary oligomerization, in particular of a wide fraction of the charge, makes it possible to optimize the yields, the conversion, and the selectivity for propylene, relative to direct cracking. It also makes it possible for cracking to be carried out in a fixed, moving, or fluidized bed, optionally with co-production of oligomers for uses other than the production of propylene.

18 Claims, 2 Drawing Sheets

PROCESS FOR MULTISTAGE CONVERSION OF A CHARGE COMPRISING OLEFINS WITH FOUR, FIVE OR MORE CARBON ATOMS, WITH THE AIM OF PRODUCING PROPYLENE

The invention relates to a process for production of propylene starting from light hydrocarbon fractions in particular comprising butenes and/or pentenes.

It relates more particularly to a process by which an olefinic charge, i.e. comprising olefins, hydrocarbons in which the number of carbons is greater than or equal to 4, for example a C4 and/or C5 fraction (with the term Cn indicating a hydrocarbon cut with n carbon atoms), for example from steam cracking or from FCC, can be converted at least partially to propylene. The term FCC, the abbreviation of the expression Fluid Catalytic Cracking, denotes fluidized-bed catalytic cracking. In general, and according to the present invention, the term FCC denotes the conventional process used in the refinery, of catalytic cracking of heavy petroleum fractions, using a charge mainly boiling above approximately 350° C. (at least 50 wt. %, generally at least 70 wt. % and often 100 wt. % of the charge boiling above 350° C.), for example vacuum distillate, or optionally atmospheric residue.

These C4/C5 olefinic cuts are available in large, often surplus quantity, in oil refineries and steam cracking installations. However, their recycling is problematic:
  their recycling to steam cracking presents problems (the yields of light olefins are lower than with the paraffinic cuts and they have high coking tendency),
  their recycling to FCC can scarcely be envisaged as they are very unreactive in the conditions of FCC, which are adapted to the vacuum distillate charge. Their recycling to FCC would therefore require the use of harsher conditions or specific catalysts, which would alter the operation of FCC.

The charge of the process according to the invention can also comprise a steam cracked gasoline or an FCC gasoline, or some other olefinic gasoline. (By gasoline is generally meant a hydrocarbon cut obtained for the most part at least from at least one conversion or synthesis unit (such as FCC, visbreaking, coking, Fischer-Tropsch unit, etc.) and where the largest proportion and typically at least 90 wt. % of this cut is comprised of hydrocarbons having at least 5 carbon atoms and a boiling point less than or equal to approximately 220° C.).

The olefinic cut constituting the charge of the process is therefore preferably selected from those defined previously, or comprises a mixture of those defined previously. A typical charge often comprises butenes and/or pentenes in notable or considerable quantity, but can also comprise ethylene, optionally small quantities of unfractionated propylene, hexenes, olefins having from 7 to 10 carbon atoms, and olefinic gasoline cuts. Most often, the charge is not purely olefinic but also comprises paraffins (in particular n-butane and/or isobutane, pentanes, and sometimes aromatics, in particular benzene and/or toluene, and/or xylenes. It can comprise isobutene and/or iso-amylenes.

The charge also often comprises highly unsaturated compounds: dienes (diolefins) in particular with 4 or 5 carbon atoms (especially butadiene).

The charge is typically a light charge, whose final distillation point (according to the TBP process, well known to a person skilled in the art), or at least the point at which 90 wt. % of the charge is distilled, is very generally below 320° C., and generally below 250° C.

The process for conversion of a charge comprising C4 and/or C5 olefinic hydrocarbons, to a cut comprising propylene, the object of the present invention, uses the series of the following stages successively:
  a stage of oligomerization and/or co-oligomerization of the butenes and/or pentenes contained in the charge, in particular to obtain higher olefins, in particular with number of carbon atoms for the most part greater than or equal to eight. If the charge, according to a variant of the process according to the invention, comprises ethylene, the reactions of co-oligomerization can also produce a certain quantity of C6 or C7 olefins,
  a stage of catalytic cracking of the higher olefins thus produced.

Often, compounds formed by the addition of n identical olefins are called oligomers of olefins, and compounds formed by the addition of n olefins of which at least two are different are called co-oligomers.

According to the invention, and hereinafter in the present description as well as in the claims, the term oligomers (and the terms oligomerize and oligomerization) will be used more widely, applying it to higher olefins formed by addition of n identical and/or different olefins (the term thus also applying to a cut comprising co-oligomers).

Oligomerization differs from polymerization by addition of molecules in limited number, the aforementioned figure n being, for the most part by weight at least oligomers, comprised between 2 and 10, inclusive, and generally between 2 and 5, in particular between 2 and 4. The oligomers may however comprise traces of olefins that have been oligomerized with n>10. Generally these traces represent less than 5 wt. % relative to the oligomers formed.

The installation for applying the process according to the invention is preferably installed near or on a refining site (oil refinery), or a petrochemical works (generally steam cracker).

Prior Art:

A known process for production of propylene, apart from the conventional processes for production of FCC and steam cracking (in which propylene is a co-product with other products such as in particular gasoline or ethylene), is the process for metathesis which converts an ethylene+n-butene mixture to propylene. This process is described in French patent FR 2 668 595.

One of the advantages of the process according to the invention, relative to metathesis, is that it produces propylene from all of the olefinic compounds of the C4 and C5 cuts and optionally of hydrocarbon cuts with a larger number of carbon atoms, in particular gasoline, and does not require massive consumption of ethylene, which is a high-cost product. If it is applied at a steam cracking site, the process according to the invention not only makes it possible not to use ethylene as charge, but also to co-produce ethylene with the propylene. As the co-production of ethylene is typically less than that of propylene, this makes it possible to improve the propylene to ethylene ratio of the steam cracker.

Moreover, if it is applied in an oil refinery, the process according to the invention makes it possible conversely to valorize as necessary (in addition to C4/C5 cuts) relatively limited and/or difficultly valorizable quantities of ethylene, which is often the case in the refinery.

Single-stage processes for production of propylene from C4 and C5 olefinic cuts are also known:
  in particular a process is known that consists essentially of fluidized-bed catalytic cracking, by technology close to conventional FCC, but operating in conditions of high temperatures and high severity, in particular: temperature at riser outlet close to 700° C. ("riser" is the vertical rising pipe with ascending circulation of catalyst and reaction charge). A drawback of this type of process, sometimes called petrochemical FCC, is that it produces overcracking of the gasoline contained in the charge which thus lowers the yield of the latter. The paraffins contained in the charge are also subject to severe temperature conditions, which can cause thermal cracking and the formation of light compounds which are poorly valorizable by this process, for example compounds lighter than propylene. Moreover, the declared propylene yield barely exceeds 30%, even in conditions of very high severity.

Another process for production of propylene is a fluidized-bed process using a zeolite ZSM-5 as catalyst. This process is described in international application WO 01/04237 as well as in the article "Maximizing Refinery Propylene Production Using ZSM-5 Technology", which appeared in the journal "Hart's Fuel Technology and Management", issue of May 1998. The typical operating conditions of this process are a temperature in the region of 600° C., and a pressure from 0.1 to 0.2 MPa. In these conditions, the propylene yield is approximately 30% and can rise to 50% with recycling of the unreacted C4 and C5 cuts.

A drawback of this process is that it is quite demanding in terms of severe operating conditions, and the definition of the incoming cuts, olefinic C4 and C5, which cannot be gasolines with number of carbon atoms greater than 5, as in the case of the present invention which can treat a gasoline cut. Another drawback is that the paraffins in the charge, which pass through the reactor without being converted catalytically, can be cracked partially, in particular thermally, with undesirable formation of light compounds.

In the family of single-stage processes, a process described in the article "Production of Propylene from Low Valued Olefins", which appeared in the journal "Hydrocarbon Engineering" of May 1999 can also be mentioned. This is a fixed-bed process in which the catalyst is a type ZSM-5 zeolite acting in the presence of steam. The temperature is close to 500° C. and the pressure is comprised between 0.1 and 0.2 MPa. The declared cycle time is of the order of 1000 hours. The catalyst is regenerated in situ and its total life, i.e. the length of time it is used in the reactor before it is renewed completely, is approximately 15 months. The declared propylene yield is approximately 40% and could rise to 60% with recycling of the unreacted C4 and C5 cuts. This process makes it possible to obtain a relatively high propylene yield. However, it requires the use of steam, and the catalyst cycle time is not very high.

A process described in international application WO 99/29805 and in patent EP-A-1 061 116 can also be mentioned. This is a process using a type MFI zeolite catalyst with a high Si/Al ratio (from 180 to 1000) to limit the hydrogen transfer reactions which are responsible for the production of dienes and aromatics. The temperature is close to 550° C., the pressure is close to 0.1 MPa, and the space velocity is comprised between 10 h$^{-1}$ and 30 h$^{-1}$. The propylene yield is comprised between 30 and 50%, relative to the quantity of olefins contained in the charge. It can therefore be estimated at typically less than 30% referred directly to the incoming charge.

A process described in patent EP-B-0 109 059 can also be mentioned. This is a process using a type ZSM-5 or ZSM-11 zeolite catalyst possessing special characteristics, used with a high space velocity. This process also describes in one variant, the sequence of oligomerization of a C4 cut, removal of unreacted butanes, and catalytic cracking of the oligomers. The purpose of the oligomerization is removal of the butanes before the cracking stage, via an oligomerization of the butenes facilitating butanes/oligomers fractionation whereas butanes/butenes fractionation is difficult. The olefinic C5 cuts are cracked directly. There is no mention of technical means or special process arrangements when the charge comprises isobutene and/or isopentene, and/or isoamylenes.

Finally, U.S. Pat. No. 6,049,017, which describes a process for production of propylene and ethylene from olefinic C4 cuts comprising a stage of removal of isobutene by etherification can also be mentioned. In the process according to the present invention, the removal of isobutene, even if it is possible or preferable, is not indispensable, as will be explained later.

DETAILED DESCRIPTION OF THE INVENTION

In general, relative to single-stage processes for conversion that use a single catalyst and a single set of operating conditions, the process according to the invention, which uses two separate stages, makes it possible to increase the chain length of the olefins before they are sent to the cracking stage so as to make them more reactive to said cracking, and to optimize each of the stages from the standpoint of the catalyst and the operating conditions, as will be discussed in more detail later.

The different operating conditions make it possible, in particular in the oligomerization stage, to promote the reactions of addition, in particular by using a relatively high pressure, whereas it is preferable to use a relatively low pressure and a higher temperature for the cracking stage. Thus, in particular, the propylene formed in the cracking stage has very little tendency to oligomerize once formed.

It has also been found that preliminary oligomerization of a charge comprising both C4 olefins and at least a notable quantity of other olefins of the group comprising C2, C5 and C6 olefins, in particular C5 and/or C6, would lead to increased yields and to better selectivity for propylene.

In particular, oligomerization (probably with partial co-oligomerization) of a mixture comprising C4 and C5 olefins, or C4 and C5 and C6, or C4 and C2 and C5, leads to improved propylene yields (after cracking), to greater conversion, and to operating conditions which are easier to apply, than if only the C4 cut was oligomerized, the C5 olefins in particular being cracked without preliminary oligomerization. The advantage of this co-oligomerization is notable when the quantity of C5 cut oligomerized is sufficient.

Among the preferred charges of the process according to the invention, which are fed to the oligomerization stage b), charges are found comprising at least 50 wt. % and often at least 70 wt. % or even more of C4+C5+C6 fractions, and which comprise olefins of at least two of the fractions C4, C5, and C6, and in particular a charge:

comprising an olefinic C4 cut (i.e. comprising olefins, optionally with other compounds, for example paraffins), the charge comprising for example at least 10 wt. % of C4 olefins, and also comprising C5 and/or C6 olefins, for example at least 10 wt. %, with a mass ratio:

$R1$=C5 Olefins+C6 Olefins/C4 Olefins which is greater than 0.15 and for example 0.2<$R1$<5 in particular 0.3<$R1$<3 and in particular 0.5<$R1$<2 and more particularly 0.7<$R1$<1.5.

or comprising an olefinic C4 cut, the charge comprising for example at least 10 wt. % of C4 olefins, and also comprising C5 olefins, for example at least 10 wt. %, with a mass ratio:

R2=C5 Olefins/C4 Olefins greater than 0.15 and for example 0.2<R2<5 in particular 0.3<R2<3, in particular 0.5<R2<2 and more particularly 0.7<R2<1.5.

These charges comprising C4 and C5 olefins can also comprise C6 olefins; they can also be practically free from C6 olefins, with for example a mass ratio:

R3=C4 Olefins+C5 Olefins/C6 Olefins greater than 10, the C6 olefins being sent for example to the cracking stage, mixed with the oligomers, without being subjected to preliminary oligomerization.

These charges give good propylene yields, after oligomerization and cracking according to the process of the invention. It is thought that the C4 and C5 olefins, in particular the fractions of C9 co-dimers, resulting from dimerization of a butene and of a pentene give better propylene yields and a higher propylene/ethylene ratio than by direct cracking of C4 or C5 olefins, in particular because a notable fraction of C9 dimer can crack giving 3 molecules of propylene.

The fractions resulting from catalytic cracking of the oligomers typically contain relatively small quantities of olefinic C4 and C5 cuts. The majority of the charge is typically an external olefinic fraction, of fresh charge, i.e. not received from the effluents of Stage d) of the process according to the invention, for example one or more charges received from the effluents of a steam cracker (cracking naphtha for example), and/or from an FCC mainly cracking vacuum distillate. This means in particular that it is possible to oligomerize a charge comprising a sufficient quantity of C5 olefins, complying with the values of the ratios R1 and R2 given above.

The process according to the invention leads to several advantages:

Greater flexibility in the choice of charges: not only olefinic C4 cuts, but also with C5 and/or C6, or even C7 olefinic fractions, and optionally ethylene, which can be the feed for oligomerization and/or relatively heavy olefinic gasoline that can easily be introduced in the cracking stage.

A higher propylene yield.

A higher propylene/ethylene ratio.

A higher degree of conversion in the cracking stage, owing to the increased reactivity of the oligomers.

A longer cycle time of the cracking catalysts (and of the oligomerization catalysts), it being possible to carry out cracking in milder conditions, in particular at a lower temperature. This longer cycle time means that one or more fixed-bed or moving-bed catalytic cracking reactors can be used without operational problems, and the use of the more expensive fluidized-bed reactors can be avoided.

The invention therefore proposes a process for catalytic conversion of a hydrocarbon charge comprising olefins with 4 and/or 5 carbon atoms, said process being characterized by the following succession of stages:

at least one Stage b) or b1) or b3) of oligomerization (the Stages b), b1) and b3) will be explained later), in which a catalytic oligomerization of the olefins with 4 and/or 5 carbon atoms contained in the charge, to higher olefins, i.e. to oligomers having a number of carbon atoms for the most part greater than or equal to eight, is carried out in at least one reactor, then, a Stage d) in which catalytic cracking of at least a proportion, generally a substantial proportion (such as at least 20 wt. % or at least 30 wt. %), and often the greater proportion (more than 50 wt. %, often more than 70%, or even 100%) at least of the oligomers produced, is carried out in a reactor separate from the oligomerization reactor, to produce in particular propylene.

Before the charge is introduced into the unit, it will preferably be possible for it to undergo selective hydrogenation first, in a Stage a) in order to remove the diolefins and other acetylenic impurities which are often present in the charge. It has in fact been found that these various highly unsaturated compounds contribute to a certain deactivation of the oligomerization catalyst and that the selective hydrogenation makes it possible to increase the quantity of olefins that can be converted.

According to a variant of the process according to the invention, the effluent from the oligomerization stage b) is subjected to a fractionation stage c) comprising a distillation for separating at least a proportion of the compounds with 4 and/or 5 carbon atoms, which is often evacuated directly without feeding the catalytic cracking reactor. The C4/C5 fraction that did not react to oligomerization is in fact essentially paraffinic and has very low reactivity to catalytic cracking. Its direct evacuation avoids passage through the catalytic cracking reactor which can give rise to the undesirable production of gas owing to a certain level of thermal cracking. This C4/C5 charge can be sent to a steam cracking unit, as this paraffinic charge has proved to be a good charge for steam cracking.

It is also possible to evacuate the C6 fraction and/or the C7 fraction from the effluent from oligomerization stage b), and-optionally send it to steam cracking, as well as the C3-fraction compounds with 3 carbon atoms or less of these same effluents from oligomerization.

The effluent from the catalytic cracking stage d) is typically subjected to a fractionation stage e) most often comprising compression of the gases and one or more distillations for separating the effluents and producing a propylene-rich C3 cut, or practically pure propylene.

A proportion of the compounds with 4 and/or 5 carbon atoms contained in the effluents from cracking can advantageously be recycled to the inlet of Stage b) or of Stage a).

The particular conditions of the various reaction stages of the process according to the invention are described in more detail below, according to a variant comprising a selective hydrogenation, an oligomerization and a catalytic cracking integrated on a single site, the charge used being a light cut of C4 and C5 hydrocarbons mainly containing butenes, pentenes, butanes, pentanes as well as, in certain cases, butadiene and pentadiene in variable quantity.

1) Selective Hydrogenation (Stage a)):

The light cut comes typically from a catalytic cracker and/or a steam cracker. The contents of dienes and acetylenics are high when this cut comes from a steam cracker; that is why the stage of selective hydrogenation of the dienes and acetylenics to olefins is almost indispensable in this case. It is also preferable in the majority of cases, as it reduces the coking of the oligomerization catalyst in Stage b), and increases the cycle time of the oligomerization reactor. However, the scope of the invention would not be exceeded if said stage of selective hydrogenation were not included in the process according to the invention.

The main aim of this first stage is to convert the diolefins (or dienes) to mono-olefins. In fact, the mono-olefins are the source of the oligomers produced in Stage 2. It is therefore desirable to convert the diolefins to mono-olefins. The second aim of this stage is to remove the traces of acetylenic hydrocarbons which are always present in these cuts and are undesirable compounds for oligomerization, these compounds also being converted to mono-olefins.

When there is a high proportion of diolefins in the cut, the conversion can be carried out advantageously in two or three reactors in series for better control of the selectivity of hydrogenation. Often the charge to be treated by recycling is diluted with a certain quantity of the effluent from this selective hydrogenation.

The residual content of diolefins+acetylenics of the effluent from selective hydrogenation is typically less than approximately 1000 ppm by weight, preferably less than approximately 100 ppm by weight and very preferably less than 20 ppm by weight. The residual content of acetylenics can even be less than 10 ppm, or 5 ppm or even 1 ppm by weight.

The quantity of hydrogen required for all of the reactions carried out in this stage is generally adjusted as a function of the composition of the cut so as to have advantageously just a slight excess of hydrogen relative to the stoichiometric.

Generally, this stage of selective hydrogenation is carried out using a catalyst comprising at least one metal selected from the group formed by nickel, palladium, and platinum, deposited on a support comprising alumina, silica or silica-alumina. Preferably a catalyst is used which comprises at least palladium or a palladium compound fixed on a refractory mineral support, for example on an alumina or a silica-alumina. The content of palladium on the support can be typically from 0.01 to 5 wt. %, preferably from 0.05 to 1 wt. %. Various forms of pretreatment known to a person skilled in the art can optionally be applied to these catalysts to improve their hydrogenation selectivity towards the mono-olefins.

The operating temperature of selective hydrogenation is generally comprised between 0 and 200° C., the pressure is typically comprised between 0.1 and 5 MPa, often between 0.5 and 5 MPa, the space velocity is typically between 0.5 and 20 $m^3$ per hour per $m^3$ of catalyst, often between 0.5 and 5 $m^3$ per hour per $m^3$ of catalyst, and the molar ratio H2/(acetylenic+diolefinic compounds) is generally comprised between 0.5 and 5 and preferably between 1 and 3.

When a gasoline cut is also used as the feed for catalytic cracking, this cut can also be subjected beforehand to selective hydrogenation, jointly with or separate from that of the C4 and/or C5 cut. When this selective hydrogenation is carried out jointly, the gasoline can optionally be separated from the C4 and/or C5 cut upstream of the oligomerization.

Selective hydrogenation is generally carried out using a fixed-bed reactor, with descending co-current flow of the charge to be treated and of the hydrogen, or with descending flow for the charge to be treated and ascending flow for the hydrogen.

The process of the invention can also comprise one or more optional stages of purification of the charge (separate from or jointly with the selective hydrogenation) upstream of the oligomerization, which may be useful or necessary for at least one of the following stages: oligomerization and cracking. The usefulness of these optional stages of purification is directly dependent on the catalyst or catalysts used as well as on the operating conditions and will be obvious to a person skilled in the art for each particular case considered. Thus, the scope of the invention would not be exceeded if, upstream of the oligomerization, one or more stages of desulphuration, and/or drying, and/or denitrogenation, and/or deoxygenation, were carried out to remove one or more of the following impurities: sulphur, water, nitrogen, oxygen, below 100 ppm, or 10 ppm, or even 1 ppm by weight, in accordance with conventional techniques.

2) Oligomerization (Stage b)):

The aim of the second stage is to oligomerize the linear, and optionally branched, C4 and C5 olefins, as well as any other olefins present, for example and non-limitatively C2 olefins (ethylene) and/or C6 olefins (hexenes), resulting from the preceding stage, to obtain a mixture of hydrocarbons containing mono-olefins with a number of carbon atoms for the most part greater than or equal to eight. Typically, starting from a C4 charge, oligomers are obtained in which the number of carbon atoms is to a large extent at least less than or equal to 30, and for the most part between 8 and 20.

Oligomerization can be carried out in one or more stages, with one or more reactors and one or more catalysts. The following description of the catalyst and of the operating conditions can apply to any one of the stages and/or to any one of the reactors.

The oligomerization stage can use a catalyst comprising a Lewis acid, for example aluminium chloride, a chloroalkylaluminium, tin tetrachloride, boron trifluoride, said Lewis acid often being combined with traces of hydrochloric acid, water, tert-butyl chloride, or organic acids.

The selectivities for dimer and for trimer depend of the catalyst and on the operating conditions. In the present invention, the process for oligomerization is such that a notable or if necessary thorough conversion of all of the starting olefins is sought.

The catalyst used for the oligomerization stage can also comprise supported sulphuric acid or supported phosphoric acid, for example on silica, alumina, or silica-alumina.

The catalyst used for the oligomerization stage can also comprise a sulphonic resin (as a non-limiting example, an AMBERLIST resin marketed by the company ROHM & HAAS).

The catalyst used for the oligomerization stage can also comprise a silica-alumina, or preferably an acid solid exhibiting shape selectivity.

For example, said catalyst can comprise at least one zeolite exhibiting shape selectivity, said zeolite comprising silicon and at least one element chosen from the group comprising aluminium, iron, gallium, phosphorus, boron, and preferably aluminium. Said zeolite can for example be of one of the following structural types: MEL (for example ZSM-11), MFI (for example ZSM-5), NES, EUO, FER, CHA (for example SAPO-34), MFS, MWW, or can also be one of the following zeolites: NU-85, NU-86, NU-88 and IM-5, which also exhibit shape selectivity.

The advantage of these zeolites which exhibit shape selectivity is that it limits the formation of highly branched oligomers, for example tri-branched isomers, cracking of which leads to a lower propylene/isobutene selectivity, i.e. to a lower propylene isobutene mass ratio.

It is also possible to use several zeolites exhibiting shape selectivity, for example a type MFI zeolite (for example ZSM-5) combined with another zeolite, previously mentioned or of one of the types previously mentioned.

The zeolite used can also be mixed with a zeolite that does not exhibit shape selectivity, for example a zeolite Y of structural type FAU.

The zeolite or zeolites can be dispersed in a matrix based on silica, alumina or silica-alumina, the proportion of zeolite (and generally of zeolite exhibiting shape selectivity) often being comprised between 3 and 80 wt. %, in particular between 6 and 50 wt. % and preferably between 10 and 45 wt. %.

The zeolite used (or the zeolites used) exhibiting shape selectivity generally have an Si/Al ratio greater than 12, preferably greater than 40, more preferably greater than 50, and even more preferably greater than 80.

The Si/Al ratio can for example be comprised between 40 and 1000. This makes it possible to reduce the acidity of the catalyst and the reactions of hydrogen transfer which lead to the formation of paraffins having little or no reactivity in the subsequent cracking stage. These high Si/Al ratios can be obtained at the time of manufacture of the zeolite, or by subsequent dealumination.

The oligomerization catalyst can finally be different from the aforementioned catalysts, if it possesses notable activity in oligomerization.

The catalyst can be used in the solid state, in powder form, or in the form of spheres or extrudates with diameter generally comprised between 0.4 and 6 mm, and preferably between 0.6 and 4 mm.

The catalyst can also be used in the form of a suspension in a saturated hydrocarbon such as hexane or isobutane, or in a halogenated hydrocarbon such as methyl chloride. The suspension can be used in a bubbling bed, in particular with particles with average diameter comprised between 0.25 and 1 mm and preferably between 0.3 and 0.8 mm, or in fine suspension, with particles of average diameter between 0.02 and 0.25 mm and preferably comprised between 0.03 and 0.20 mm. It is also possible to use a suspension where the particles are in the colloidal state.

The preferred form of application for the oligomerization reactor is fixed-bed.

The operating conditions are chosen as a function of the catalyst, in such a way that the reaction takes place at a sufficient rate. The temperature (at reactor outlet) can be for example comprised between −100° C. and 350° C., preferably between 0° C. and 310° C., and very preferably between 70° C. and 310° C., for example between 120° C. and 250° C., in particular between 150 and 220° C. Often the temperature of the oligomerization stage b) is at least 40° C. lower, preferably at least 80° C. lower, and very preferably at least 120° C. lower than that of the catalytic cracking stage d).

The pressure is typically comprised between 0.1 and 10 MPa, and preferably comprised between 0.1 and 5 MPa, and very preferably comprised between 0.8 and 4 MPa, and in particular comprised between 1.5 and 3.5 MPa. Often the pressure (at reactor outlet) of the oligomerization stage b) is at least 0.5 MPa higher, preferably at least 1 MPa higher, and very preferably at least 1.5 MPa higher than that of the catalytic cracking stage d).

The SV is generally comprised between 0.1 and 5 m$^3$ per hour per m$^3$ of catalyst, and preferably between 0.5 and 4 m$^3$ per hour per m$^3$ of catalyst.

The operating conditions are often also optimized as' a function of the characteristics of the charge.

It is also possible to use, for the selective hydrogenation stage a) and for the oligomerization stage b), conditions which are similar, and in particular pressures which are similar, such as pressures that only differ from one another by 0.5 MPa at most, or even 0.3 MPa at most. This makes it possible for the two reactions to follow one another, optionally without intermediate fractionation or pressurization or depressurization, or optionally even without intermediate cooling or even without intermediate heating. It is also possible to carry out the reactions of selective hydrogenation and of oligomerization in two successive beds of the same reactor. The conversion of the C4 and C5 olefins during oligomerization generally reaches 70%, or 90% or more, and can even be practically total.

It may be useful in this stage, in the particular conditions discussed below, to add a small quantity of ethylene to the charge as this promotes the formation of oligomers with six or seven carbon atoms (by addition with the C4/C5 olefins of the charge) and their subsequent cracking to propylene. This makes it possible to valorize the relatively limited quantities of ethylene available in an oil refinery (said ethylene essentially being produced in FCC). Another situation where this arrangement is useful is that of an ethylene supply from a steam cracker, during economic conditions when there is low demand for ethylene but the demand for propylene remains high. The quantity of ethylene can then be adjusted to the available surplus. (For comparison, such adjustment is not possible in the process with metathesis, where as many moles of ethylene are used as of butene). The quantity of ethylene that can be used is for example comprised between 0.5 and 15 wt. % of the oligomerization charge. Typically, the charge of the oligomerization reactor comprises 0.5 to 15 wt. % of ethylene relative to the sum of the C4, C5 and C6 olefins.

The use of oligomerization at relatively high pressure and low temperature relative to that of catalytic cracking makes it possible to optimize the two types of chemical reactions separately, and to use specific catalysts. It also makes it possible to increase the cycle time and life of the oligomerization catalyst, which is subject to far less severe conditions, in particular with respect to coking.

Generally, the oligomerization reactor is a fixed bed, uses a catalyst comprising a silica-alumina or preferably at least one zeolite, and very preferably a zeolite exhibiting shape selectivity (for example a type MFI zeolite), and operates at a temperature comprised between 70° C. and +310° C., a pressure typically comprised between 0.1 and 5 MPa, and a space velocity comprised between 0.1 and 5 m$^3$ per hour per m$^3$ of catalyst.

According to a variant of the process according to the invention, which can be used in particular when the charge contains isobutene, especially in substantial or high quantity, the oligomerization stage b) can be carried out in 3 stages:

A Stage b1) of limited oligomerizatiori, making it possible to carry out preferential oligomerization of the more reactive branched olefins, in particular of isobutene, the linear olefins being in particular less oligomerized, A Stage b2) of fractionation of the effluents from Stage b1), for example by distillation or any other known fractionation, making it possible to extract at least one cut comprising di-isobutene and/or, optionally, tri-isobutene: C8 cut rich in di-isobutene, or practically pure di-isobutene, or optionally a C8+ cut (C8 and heavier, optionally also comprising tri-isobutene at the same time as di-isobutene), said extracted cut being evacuated directly (i.e. not being fed to the subsequent Stages b3) of oligomerization and d) of cracking).

A Stage b3) of final oligomerization of the effluent from Stage b2), or at least of olefinic C4 and/or C5 fractions, after evacuation of the aforementioned cut comprising di-isobutene and/or optionally tri-isobutene.

These stages interact with one another as well as with cracking stage d): Stages b1) and b2) make it possible to remove at least partly the isobutene via a product: di-isobutene and/or tri-isobutene for which the catalytic cracking propylene yields are relatively low, and obtain less-branched oligomers in Stage b3), giving better cracking yields in Stage d). The at least partial removal of isobutene before Stage b3) also makes it possible to reduce gum formation in said Stage b3) where deep oligomerization of the linear C4 and/or C5 olefins is required.

The variant of the process described above (with limited oligomerization b1) then final oligomerization b3) after fractionation b2) and at least partial removal of the oligomers formed in b1)) can also be applied to a charge comprising isoamylenes (branched C5 olefins) instead of isobutene, or a charge comprising isobutene and isoamylenes. These branched olefins can be oligomerized much more easily and preferentially to their linear homologues, which makes it possible to remove them at least partially after Stage b1).

Stage b1), which does not aim at the formation of linear olefins which are good precursors of propylene, can be implemented with a catalyst among those mentioned previously, but also with a zeolite catalyst having a percentage of zeolite exhibiting shape selectivity lower than that of Stage b3), or even with a non-zeolite catalyst, essentially comprising an amorphous silica-alumina of medium acidity.

Stage b1) of oligomerization can also use different, very selective operating conditions as it provides very preferential or exclusive oligomerization of the isobutene (and/or of the isoamylenes) relative to the n-butenes (linear butenes) and/or the n-pentenes. For example, it will be possible to use milder conditions in the first stage of oligomerization relative to the final stage, in particular by using a temperature at least 40° C. lower in the first stage. It is for example possible to carry out a first oligomerization b1) with a temperature comprised between 20 and 80° C., and a second oligomerization b3) with a temperature above 100° C., or even 120° C. or more. It is possible to use the same catalyst for 3), for example based on silica-alumina, or alternatively different catalysts.

Di-isobutene and tri-isobutene are in fact, for each of these compounds, a mixture of isomers, well known to a person skilled in the art; in particular there are two isomers for di-isobutene, including 2,4,4-trimethyl-2-pentene, with normal boiling point of 104.9° C., which boils in the gasoline range and has a good octane number. Tri-isobutene comprises oligomers some of which have a normal boiling point comprised between 196 and 210° C., which can be incorporated at least partly in a gasoline base or a kerosene, or a gasoil, depending on the valorizations required. It can also be valorized for uses in the chemical industry.

An extracted cut rich in di-isobutene can be valorized at a high level as gasoline base, or for other uses, for example in the chemical industry etc.

Stage b1) can in particular be applied on a C4 cut alone; a C5, or C2 and C5 cut can then be added if necessary to the butenes not converted in b1) for final oligomerization in Stage b3). It is also possible to carry out Stage b1) with a charge comprising hydrocarbons other than a C4 cut, for example an olefinic cut with C4 and C5, or C4 and C5 and C6, or C4 and C2, or C4 and C2 and C5, or C4 and C2 and C5 and C6.

When oligomerization is applied in a single Stage b), it is also possible, in the same way as after Stage b1), for a proportion of the oligomers produced for example a fraction comprising di-isobutene and/or tri-isobutene, to be removed and evacuated directly.

In all these variants, it will also be possible to evacuate unreactive C4 and/or C5 fractions after a fractionation stage b2) or c), so as not to obstruct the subsequent stages.

3) Catalytic Cracking (Stage d)):

The charge fed in Stage d) of catalytic cracking typically contains from 20 to 100 wt. % of olefins with at least 8 carbon atoms that were produced by oligomerization of light olefins with 4 and/or 5 carbon atoms, often from 30 to 100 wt. %, and most often from 50 to 100 wt. %, in particular from 60 to 100 wt. %.

The charge can also comprise other oligomers formed essentially from the group comprising C2 to C10 olefins, the total quantity of oligomers with at least 6 carbon atoms being typically from 25 to 100 wt. %, often from 35 to 100 wt. %, most often from 55 to 100 wt. %, and in particular from 65 to 100 wt. % relative to the charge of Stage d).

The C6 oligomers, formed in particular by addition of ethylene to a butene, or the heavier oligomers formed at least partly from C6 and higher olefins (C6+) are in fact also good propylene precursors, which it is also advantageous to use as feed for catalytic cracking.

The catalyst used for the catalytic cracking stage can comprise a silica-alumina. Preferably, however, an acid solid exhibiting shape selectivity is used.

For example, this catalyst can comprise at least one zeolite exhibiting shape selectivity, said zeolite comprising silicon and at least one element selected from the group formed by aluminium, iron, gallium, phosphorus, boron, and preferably aluminium. Said zeolite exhibiting shape selectivity can be of one of the following structural types: MEL (for example ZSM-11), MFI (for example ZSM-5), NES, EUO, FER, CHA (for example SAPO-34), MFS, MWW, or can also be one of the following zeolites: NU-85, NU-86, NU-88 and IM-5, which also exhibit shape selectivity.

The advantage of these zeolites exhibiting shape selectivity is that it leads to better propylene/isobutene selectivity (higher propylene/isobutene ratio in the effluents from cracking).

It is also possible to use several zeolites exhibiting shape selectivity, for example a zeolite of the MFI type (for example ZSM-5) combined with another zeolite exhibiting shape selectivity, mentioned above or of one of the types mentioned above.

The zeolite or zeolites exhibiting shape selectivity, from the group comprising the zeolites of one of the following structural types: MEL (for example ZSM-11), MFI (for example ZSM-5), NES, EUO, FER, CHA (for example SAPO-34), MFS, MWW, or from the group of the following zeolites: NU-85, NU-86, NU-88 and IM-5, can also be mixed with a zeolite that does not exhibit shape selectivity, such as a zeolite Y of structural type FAU.

Often a catalyst is used which comprises one or more zeolites exhibiting shape selectivity, the proportion of zeolite(s) exhibiting shape selectivity being comprised between 70 and 100 wt. %, inclusive, relative to the total quantity of zeolite(s). In particular a catalyst can be used for which the proportion of zeolite(s) exhibiting shape selectivity is comprised between 80 and 100 wt. % relative to the total quantity of zeolite(s), and even a catalyst in which the zeolite or zeolites all exhibit shape selectivity.

The zeolite or zeolites can be dispersed in a matrix based on silica, alumina or silica-alumina, the proportion of zeolite (and generally of zeolite exhibiting shape selectivity) often being comprised between 3 and 80 wt. %, preferably between 8 and 70 wt. %, for example between 15 and 60 wt. %, in particular between 20 and 50 wt. %. The zeolite (or zeolites) used, exhibiting shape selectivity, generally has (have) an Si/Al ratio greater than 12, preferably greater than 20, more preferably greater than 50, and often greater than 80. It can for example be comprised between 40 and 500.

This makes it possible in particular to reduce the acidity of the catalyst and the reactions of hydrogen transfer which lead to the formation of paraffins at the expense of propylene formation.

Such high Si/Al ratios can be obtained at the time of manufacture of the zeolite, or by subsequent dealumination.

Finally the catalytic cracking catalyst can be different from the aforementioned catalysts, if it possesses a notable activity in catalytic cracking for the production of propylene.

The aforementioned Si/Al ratios may be different for the oligomerization and cracking catalysts, which permits their respective optimization.

The catalyst can be used in the solid state, as powder if using a fluidized-bed reactor, for example with an average particle size comprised between 0.02 and 0.5 mm, preferably between 0.04 and 0.15 mm. Typically, the catalyst then circulates continuously from the cracking reactor to a regeneration zone, then returns to the reactor. The technology used is then similar or identical to that of the FCC process.

Oligomers can also be cracked according to the FCC process, mixed with heavy gasoil and/or vacuum distillate (or in a separate riser). This variant is the object of a separate patent application, simultaneous with the present application. In such a case, the quantity of oligomers added to the heavy charge (heavy gasoil and/or vacuum distillate) is in most cases relatively low: typically between 3 and 40 wt. %, in particular from 4 to 30%, or from 4 to 26 wt. % of the total charge.

The charge treated is typically an olefinic cut (C4 and/or C5 and/or C6 and/or C2) obtained from FCC. In general, only a limited quantity of olefinic fraction is treated, which leads after cracking of the oligomers in the FCC (with the vacuum distillate and/or the heavy gasoil) to an increase in the quantity of gas compatible with the cracked gas compressor and the gas treatment installation and light C5/C6 fractions. The feed for oligomerization (after any purification treatments) can then be a predetermined quantity of olefinic cut (C4 and/or C5 and/or C6 and/or C2), the complement relative to the production of the FCC being evacuated and fractionated so as to produce a purge flow and prevent excessive swelling of the loop of C5 light products around the FCC and of oligomerization, in particular an accumulation of isobutene and/or isoamylenes. These compounds in fact have a tendency to oligomerize rapidly but to crack again (during the cracking stage) in notable quantity or completely back to the starting product, producing only very little propylene. A purge can prevent an increasing accumulation of isobutene and/or isoamylenes.

Alternatively, it can be used in a fixed bed or in a moving bed, in the form of spheres or extrudates with diameter generally comprised between 0.4 and 6 mm, preferably between 0.6 and 4 mm.

According to one of the preferred embodiments of the process according to the invention, a moving-bed of catalyst, for example of spheres with diameter from 1 to 3 mm, is used for the cracking stage d). The catalyst then circulates continuously or semi-continuously from the cracking reactor to a regeneration zone, then returns to the reactor.

According to another preferred embodiment, at least 2 fixed-bed reactors with cyclic operation are used, one reactor being in operation (cracking phase) and another reactor in the regeneration phase, according to the "swing" reactor technique, using the term that is well known to a person skilled in the art. When the regeneration of the second reactor is finished, the charge is swung to the second reactor, and the catalyst of the first reactor is regenerated. It is also possible to use three reactors, with two reactors in operation and one in regeneration, or three reactors in operation and one in regeneration, or N reactors in operation and P reactors in regeneration, variants which are considered according to the invention as technical equivalents to swing reactors.

The regeneration phase typically comprises a phase of combustion of the carbon deposits formed on the catalyst, for example by means of an air/nitrogen mixture or of air with lower oxygen content (for example by recirculation of fumes), or of air, and can optionally comprise other phases of treatment and of catalyst regeneration.

Catalytic cracking is usually carried out at a temperature of approximately 450 to approximately 650° C. and preferably between 480° C. and 600° C. with a residence time in the reactor of less than 1 minute, often from approximately 0.1 to approximately 50 seconds and preferably from 0.4 to 15 seconds. The operating pressure is generally comprised between 0.1 and 5 MPa, most often between 0.1 and 1.5 MPa, and preferably between 0.1 and 0.5 MPa.

The conditions for regeneration of the cracking catalyst generally use a temperature comprised between 300 and 900° C., in particular between 500 and 750° C., the pressure most often being close to the cracking pressure, or alternatively close to atmospheric pressure.

According to another embodiment of the process according to the invention, it is also possible to use the same circulating catalyst for oligomerization and cracking.

This circulation of the catalyst can be implemented in a moving bed or in a fluidized bed. The catalyst then circulates advantageously between three zones: the oligomerization zone, the catalytic cracking zone, and a third zone of catalyst regeneration, this last-mentioned zone in particular carrying out the removal of the coke deposited on the catalyst (by controlled combustion by one of the techniques known to a person skilled in the art). For example, the flow of regenerated catalyst leaving the regeneration zone can be divided into two flows, with the first feeding the oligomerization zone, and the second the cracking zone. The catalyst leaving the two reaction zones (after the reaction effluents have first been separated) can then be regenerated in the common regeneration zone.

The flow of catalyst can also feed the two reaction zones successively (oligomerization then cracking, or vice versa).

The flows of catalyst can if necessary undergo cooling, in particular the flow feeding the oligomerization zone, or a different cooling, to obtain different operating temperatures in the oligomerization zone and in the cracking zone. This cooling can be obtained for example by bringing the catalyst into contact with a colder gas, or in a heat exchanger. The reaction charges can also be fed at different temperatures to achieve this result. It is also possible to operate the cracking reactor with the relatively hotter, regenerated catalyst.

The main variants of implementation of the process according to the invention are as follows:

Variant A: different catalysts for oligomerization and cracking; fixed-bed oligomerization, preferably with cyclic regeneration of the catalyst in the same reactor at spaced time intervals, or with swing reactors; fixed-bed catalytic cracking, preferably with relatively frequent cyclic regeneration with other swing reactor(s).

Variant B: different catalysts for oligomerization and cracking; fixed-bed oligomerization, preferably with cyclic regeneration of the catalyst in the same reactor at spaced time intervals, or with swing reactors; moving-bed catalytic cracking (with continuous or semi-continuous circulation of the catalyst to a regeneration zone).

Variant C: different catalysts for oligomerization and cracking; fixed-bed oligomerization, preferably with cyclic regeneration of the catalyst in the same reactor at spaced time intervals, or with swing reactors; fluidized-bed catalytic cracking (with continuous circulation of the catalyst to a regeneration zone).

Variant D: common catalyst for oligomerization and cracking; moving-bed oligomerization and cracking (with the common catalyst circulating continuously or semi-continuously between an oligomerization zone, a cracking zone, and a regeneration zone).

Variant E: common catalyst for oligomerization and cracking; fluidized-bed oligomerization and cracking (with the common catalyst circulating continuously or semi-continuously between an oligomerization zone, a cracking zone, and a regeneration zone).

Variants A, B and C can also be implemented with a catalyst suspended in a liquid for the oligomerization stage.

The preferred variants according to the invention are variants A, B and C, in particular with a fixed bed for oligomerization, and the most preferred variants are variants A and B.

Generally, the propylene yield relative to the quantity of olefins contained in the fresh charge of the process is comprised between 30 and 60 wt. %, and often between 40 and 60 wt. %.

The invention will be explained in more detail by means of the description of FIGS. 1 and 2.

FIG. 1 shows an installation for implementing the process according to the invention in a first variant with considerable integration between the stages of the process (in particular by recycling).

A C4/C5 charge obtained from a steam cracking unit (not shown in the figure) is introduced through line 1. Line 1 bis carries hydrogen or a hydrogen-rich gas which is used for the stage of selective hydrogenation, carried out in a fixed bed in reactor R1 (which can comprise 2 or 3 reaction zones in series with intermediate cooling if necessary). The charge and the hydrogen-rich gas are introduced into the hydrogenation reactor R1 via line 2. R1 is also fed with a recycling stream circulating in line 13. Reactor R1 is thus fed by two separate lines 2 and 13 in FIG. 1. It is also possible to feed the charges as a mixture through a common line. Moreover, the hydrogen can also be fed inside the reactor and not upstream of it. Such variant embodiments or equivalent technical means, which are obvious to a person skilled in the art, also apply to other reactors or separation zones shown in FIGS. 1 and 2.

The effluents from reactor R1 feed, via line 3, a fractionation zone S1 comprising a stabilization column.

The isobutene can if necessary be extracted at S1 (according to one of the techniques disclosed below or any other known techniques), to reduce the quantity or avoid the presence of isobutene in the oligomerization reactor. Isobutene in fact tends to dimerize to di-isobutene, cracking of which gives relatively low propylene yields, and leads to notable recracking to isobutene, which therefore tends to accumulate.

It is also possible to extract at least one fraction of the C8 oligomers, to reduce the quantity or largely suppress the fraction rich in di-isobutene which is subjected to cracking, either following oligomerization, or after a limited oligomerization, as was explained above.

The light products, mainly hydrogen and methane, are evacuated via line 4. The selectively hydrogenated C4 cut is introduced via line 5 into oligomerization reactor R2. A recycled olefinic cut, obtained from the effluents from the catalytic cracking stage, is optionally introduced via line 10 into the oligomerization reactor. Preferably, this cut can be sent to the selective hydrogenation stage via the aforementioned line 13, rather than to oligomerization.

The effluents from oligomerization are extracted via line 6 and introduced into a separation zone S2. Zone S2 typically comprises a set of simple and/or reactive and/or extractive distillation columns, not shown in FIG. 1: After distillation of the oligomerization effluents to recover the heavier oligomers, the residual C4/C5 cut, comprising a minority of unconverted olefinic compounds and especially paraffinic compounds, is evacuated via line 7a. The oligomers are transferred at least partly via line 8, and introduced into the catalytic cracking reactor R3.

Another proportion of these oligomers, having thus been separated from the oligomerization effluents (or from at least one oligomerization stage if there are several) by withdrawal or by one or more distillations, can be evacuated via line 7c (and is therefore removed from the fraction subjected to cracking). This makes it possible to reserve a proportion of these oligomers for uses other than the production of propylene, optionally with higher valorization. Propylene production is then less, but the size of the cracking reactor is also reduced. As an example, a proportion of the C10 to C14 oligomers can be used as bases for the manufacture of linear or non-linear alkylbenzenes, or as bases for other chemical or petrochemical applications. It is also possible to separate oligomerization effluents and evacuate one or more fractions boiling in the distillation range of gasoline, kerosene or gasoil, or domestic heating oil, which can be used as base(s) for the manufacture of these products. This evacuation of a proportion of the oligomers, which are not fed to catalytic cracking, is a notable advantage of the process according to the invention relative to the single-stage processes for conversion of light olefins to propylene, which cannot provide co-production of the oligomers. It can also contribute to the indirect elimination of isobutene, when this compound is present in the oligomerization charge, by separation, for example by distillation, and evacuation of a fraction of the oligomers comprising di-isobutene and/or tri-isobutene (comprising dimers or trimers of isobutene), for example a C8 or C8+ fraction. The fraction evacuated can be separated by fractionation of the effluents from oligomerization, for example by distillation. According to the invention, fractionation is considered in the broad sense and also covers a withdrawal of a proportion of the oligomerization effluents or of the oligomers.

An oligomer fraction and/or C4 and/or C5 cut contained in the oligomerization effluents can optionally be recycled to oligomerization reactor R2 via line 7b, said rather unreactive fraction making it possible to reduce the temperature rise in the exothermic reactor R2 (or the reactors in series if the oligomerization comprises several reactors). When oligomerization is carried out in two Stages b1) and b3), specific recycling can be carried out for each of the stages (recycling of a proportion of the effluent from the same stage).

A recycling of effluents can also be used in the stage (or stages or reactor or reactors) of selective hydrogenation, and the effluents which are recycled can be effluents from selective hydrogenation or from oligomerization, optionally with total recycling around the selective hydrogenation+ oligomerization combination.

The charge of oligomers circulating in line 8 is cracked in catalytic cracking reactor R3. Reactor R3, preferably a fixed-bed or moving-bed reactor, can optionally also be fed with a gasoline fraction introduced via line 9, so as to increase the quantity of olefins cracked at least partially to propylene. The C5 fraction of gasoline, unreactive in cracking, and optionally the $C_6$ fraction, is preferably fed with the C4/C5 charge, to be oligomerized rather than with the main proportion of the gasoline fed by line 9.

The total charge of the catalytic cracking unit therefore comprises oligomers of C4 and/or C5 olefins, and optionally gasoline and/or a quantity (generally relatively small) of ethylene. This total charge is relatively light, with at least 50 wt. % and generally 80 wt. % and even typically at least 90 wt. % (and often all) of this charge boiling below 250° C. This charge typically does not contain petroleum fractions such as vacuum distillate, and is therefore very different from the charges of the FCC units of oil refineries.

The effluents from catalytic cracking unit R3 are evacuated via line 11 and are introduced into a separation zone S3, which typically comprises a gas compressor and distillation means.

When the installation for implementing the invention is on a steam cracking site, it is very useful to be able to use the fractionation train of the steam cracker for fractionation of the products. Zone S3 in FIG. 1 therefore represents a common fractionation zone, on the one hand of the products circulating in line 11, which come from the catalytic cracking stage (of the process according to the invention), and on the other hand of steam cracking effluents fed via line 16. The effluents from catalytic cracking represent a minor fraction (less than 50 molar %, and often less than 30 molar % of the steam cracking effluents. As a variant, the effluents from catalytic cracking can be mixed with those from steam cracking not upstream of the common separation zone, but after the effluents from steam cracking have undergone primary fractionation to remove the gasoline (or at least the heavy gasoline) or even after the first stage of compression of the gaseous effluents from steam cracking.

The invention therefore also proposes a process for conversion combining a stage of steam cracking and a stage of catalytic cracking, preferably with crossed recycling, in which:
a main charge of hydrocarbons representing at least 50 wt. %, and generally at least 60 wt. % of the total charge is subjected to a stage of steam cracking,
a secondary charge of hydrocarbons representing at least 5 wt. %, and generally at least 10 wt. %, for example between 10 and 40 wt. % of the total charge (made up of the main charge and the secondary charge) is subjected to a stage of catalytic cracking d) as described previously, preferably in a fixed bed or a moving bed,
the effluents from steam cracking and from catalytic cracking are cooled,
the cooled effluents from steam cracking and from catalytic cracking are fractionated at least partly in a common fractionation zone (optionally after a separate preliminary fractionation for removing liquid fractions, most or practically all of the gaseous compounds from the effluents, in particular those comprising hydrogen and hydrocarbons comprising 3 carbon atoms or less, preferably being fractionated in a common fractionation zone), to produce at least ethylene, propylene, and at least one olefinic cut comprising C4 and/or C5, and preferably C4 and C5, olefins,
said olefinic cut is subjected to at least one stage of oligomerization b) as described previously, to produce oligomers,
at least a proportion of the oligomers is sent to Stage d),
the effluents from Stage b) are preferably fractionated, in a Stage c), into at least one fraction rich in oligomers (at least 50 wt. % o and often at least 70 wt. %, or even 90 wt. %), and at least one light fraction comprising mainly (at least 50 wt. % and often at least 70 wt. %, or even 80 wt. %) light hydrocarbons having 5 carbon atoms or less, for example a fraction which is relatively poor in olefins mainly comprising C4 and/or C5 paraffins,
a proportion at least of the light fraction from the preceding stage is preferably sent to the steam cracking stage.

The last two stages mentioned above are optional but preferred according to the invention: The formation of oligomers makes it possible for light fractions with less than 8 carbon atoms (C7–), or for example with less than 6 carbon atoms (C5–), for example a C4/C5 cut, to be separated easily by distillation. As these cuts have a low content of olefins, for example less than 20 wt. %, as a result of oligomerization of most of the olefins to heavier compounds, they constitute good steam cracking charges.

The process for conversion thus defined can also use one or more of the variants of the process according to the invention mentioned above, and for example:
use of a selective hydrogenation stage a) upstream of the oligomerization stage b),
use of extraction of isobutene prior to Stage a) or prior to Stage b), and after Stage a),
use of oligomerization in at least two stages as described previously (Stages b1), b2), b3)),
evacuation, in Stage b2) or c), of a proportion of the oligomers (proportion not sent to Stage d)), in particular of a proportion comprising di-isobutene and/or tri-isobutene
evacuation (without recycling) of a proportion of the C4 cut of the effluents from cracking, to carry out an isobutene purge.

The extraction of isobutene from recycled cut(s) can be carried out separately, or at the same time as removal of isobutene from a fresh (external) charge, for example from a cut received from FCC, in a single installation for treating the recycled cuts and the fresh charge as a mixture.

Extraction of the-isobutene can be carried out by extractive distillation, for example with a solvent which can be N-methylpyrrolidone (NMP) or dimethylsulphoxide (DMSO) or an isomer of the latter.

The extraction of isobutene, and optionally of other branched olefins, in particular isoamylenes, can also comprise an etherification of the isobutene by an alcohol, then a distillation. It is also possible to carry out a hydroisomerization with reactive distillation, for separating the isobutene from butene (butene-1 being converted to butene-2 which can be separated from isobutene).

For the extraction of branched olefins (isobutene and/or isoamylenes) upstream of oligomerization, use of one or more known processes for separation, such as liquid-liquid extractions, etherifications, or other processes such as membrane processes or using selective adsorbants optionally in simulated countercurrent, also falls within the scope of the invention.

The several technical variants of the process according to the invention, described for a combined process of steam cracking and catalytic cracking, can also be applied when the installation for implementing the process according to the invention is combined with FCC (refining site), or on a mixed site (steam cracker+FCC), or on an isolated site.

The description of FIG. 1 will now be continued: The olefinic fraction, free from isobutene, and typically comprising paraffins, is recycled to the oligomerization reactor via line 10. Preferably it is recycled to the selective hydrogenation reactor R1, via line 15 then line 13 as shown by the dashed line in FIG. 1, before being recycled to the oligomerization reactor R2.

After extracting the isobutene, it is also possible to carry out extraction of paraffins so that a cut without paraffins and without isobutene, essentially comprising linear olefins, is recycled or fed to the selective hydrogenation or oligomerization.

All or preferably a proportion of the gasoline cut obtained from catalytic cracking in Stage d) can also optionally be recycled to catalytic cracking, as is indicated by line 14, shown as a dashed line. The effluents from the catalytic cracking unit other than the recycled C4/C5 cut are evacuated via line 12 as well as via other lines which are not shown. A proportion or the whole of the C4/C5 cut contained in the effluents from cracking can also be evacuated, and not recycled.

Very generally, the charge subjected to oligomerization can comprise a C5 olefinic cut, alone or mixed with other olefinic cuts such as C4 and/or C2. It was found that better cracking results (propylene yield) were obtained by cracking oligomers formed from a C5 cut, alone or co-oligomerized with other olefins, than the non-oligomerized C5 charge. The improvement relates both to the selectivity of cracking to propylene and the single-pass conversion of the oligomers, which is increased. It is thought that this observed increase in single-pass conversion, for oligomers relative to the starting olefins, comes in particular from the increase in molecular weight, and is notable for all the olefinic charges envisaged in the present application.

According to another variant, the C4/C5 cut can be recycled without extraction of the isobutene. The raw C4/C5 charge, after selective hydrogenation, is then oligomerized in R2 and separated in S2. S2 can then comprise only a separation of the oligomers (by distillation), sent to reactor R3 via line 8, with the residual C4/C5 cut (contained in the effluents from oligomerization), essentially paraffinic, being evacuated via line 7a. It is then preferable to provide evacuation (without recycling) of a proportion of the C4 cut obtained from cracking, and/or not feed a proportion of the oligomers to the cracking stage, in order to carry out a direct or indirect purge of isobutene. This evacuation of oligomers, in particular of oligomers comprising di-isobutene and/or tri-isobutene, can also be carried out within the scope of an oligomerization in one or two stages, as has already been explained.

C6 olefinic fractions can also be recycled.

Figure 2:
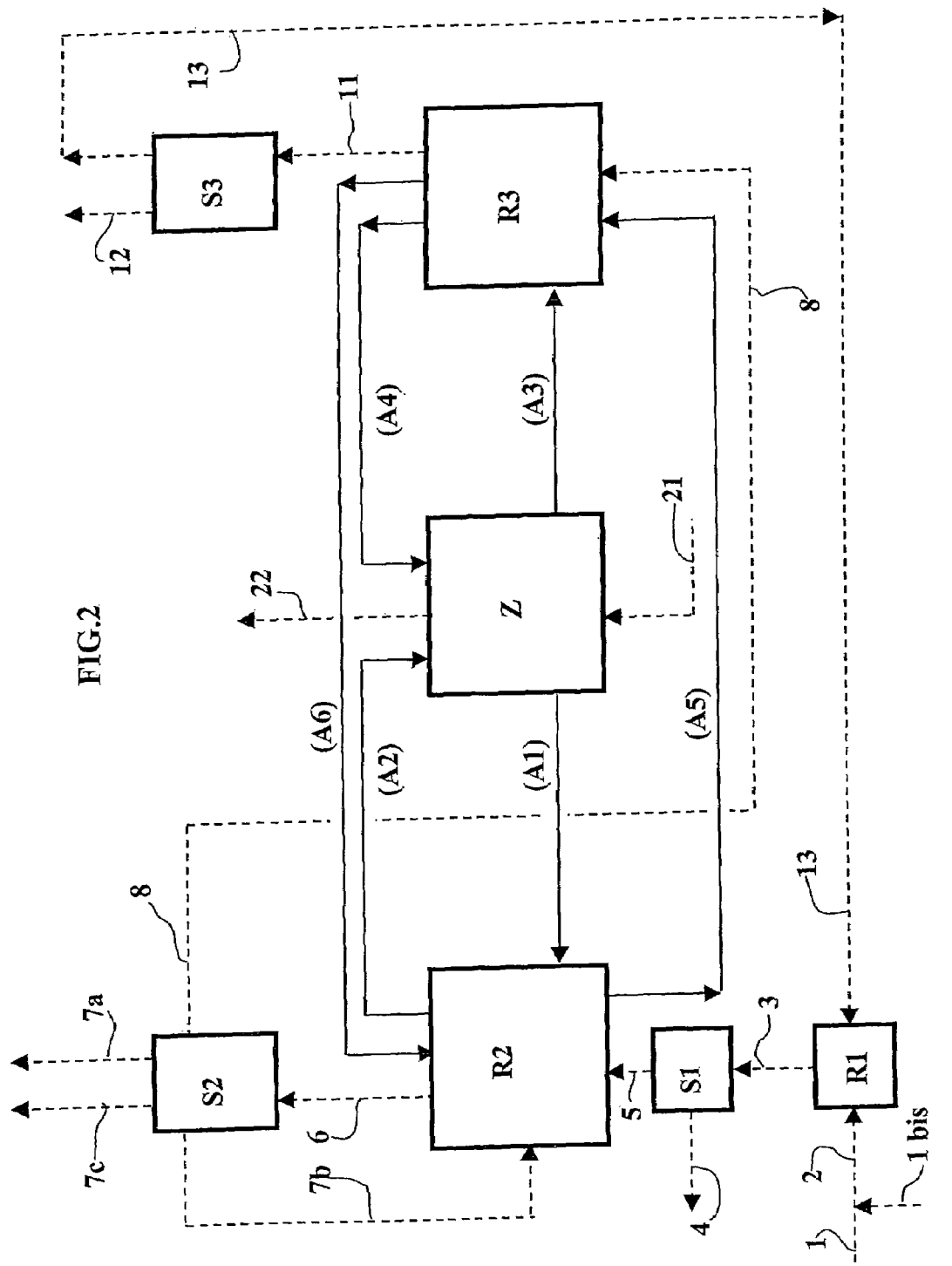

FIG. 2 describes an installation for implementing a variant of the process according to the invention using one and the same catalyst circulating in a fluidized bed in and between three separate zones: the oligomerization reactor R2, the cracking reactor R3, and a zone Z of common regeneration of the catalyst. The flows of solid are shown by solid lines and the flows of charge, effluents or various recycles are shown by dashed lines.

The catalyst is regenerated in zone Z at elevated temperatures of the order of 500° C. to 750° C., pressure levels typically comprised between 0.1 MPa and 4 MPa and preferably comprised between 0.1 and 3 MPa, by means of a combustion gas, which is generally air or air diluted with nitrogen and/or recycled combustion gas.

The air (or diluted air) is fed to zone Z via line 21 and the combustion fumes are evacuated via line 22.

In zone Z, catalyst regeneration can be carried out in one or more stages at different temperatures and oxygen partial pressures. It is thus possible to burn the coke deposited on the catalyst first with a low oxygen partial pressure, then at higher temperatures and oxygen partial pressure, without risk of the combustion reaction becoming violent, by splitting the regeneration process into two stages. Since zone Z is under an oxygen atmosphere, it is desirable to have buffer zones upstream and downstream of the said zone with inert flows, for example of nitrogen, so as to prevent any leaks of oxygen via the lines for transferring the catalyst between reactors R2, R3 and zone Z. More generally, the installation can comprise chemical engineering means which are not shown, such as catalyst hoppers, means for mixing a flow of catalyst with a liquid and/or a gas, chambers for mixing, pressurization or depressurization, wetting, or rendering inert, means for stripping, heating or cooling of the catalyst, for example a stripper of fluidized solid or a heat exchanger for heating or cooling fluidized solid etc.

A flow of regenerated catalyst is typically sent from zone Z to the oligomerization reactor R2 via transfer line A1, and returns partially deactivated from R2 to zone Z via line A2.

Similarly, another flow of regenerated catalyst is typically sent from zone Z to'the catalytic cracking reactor R3 via transfer line A3, and returns partially deactivated from R3 to zone Z via line A4.

The installation can also operate in a different mode: The whole of the regenerated catalyst can be sent to reactor R3 via line A3, then transferred from reactor R3 to reactor R2 via line A6, then returned to zone Z via line A2.

Similarly, the whole of the regenerated catalyst can be sent to reactor R2 via line A1, then transferred from reactor R2 to reactor R3 via line a5, then returned to zone Z via line A4.

The installation can also operate by combining these different modes of circulation which then use partial flows of catalyst (and not the whole of the flow of regenerated catalyst).

Attainment of lower temperatures in oligomerization reactor R2 (compared with cracking reactor R3) can be achieved by cooling (or cooling further) the flow of catalyst feeding R2 and/or by feeding R2 with reactants at relatively lower temperature. These cooling means are not shown in the figure.

The operating pressures can be similar or practically identical in the three zones: reactor R2, reactor R3, and regeneration Z to facilitate circulation of the catalyst, but it is also possible to operate at different pressures, for example at a higher pressure for oligomerization.

The other referenced elements in FIG. 2 have already been described for FIG. 1.

FIG. 2 can also represent an installation for implementing the process according to the invention with R2 and R3 operating with a moving bed, not a fluidized bed (with continuous or semi-continuous (intermittent) circulation of a catalyst in the form of particles, for example spheres with diameter comprised between 1 and 3 mm).

The process according to the invention is not limited to the elements described above, and, can be implemented according to variants or with embodiments not described in the present description but already well known to a person skilled in the art.

EXAMPLE 1

According to the Invention

The following example of application in a pilot plant illustrates the invention without limiting its scope.

A C4 cut from steam cracking, to which a C4/C5 cut recycled from the cracking stage has been added, is used as the feed for oligomerization. Said cut undergoes selective hydrogenation beforehand and removal of the isobutene that it contained initially. The compositions (as percentages by weight) of the charge and of the effluent from oligomerization are shown in Table 1.

The operating conditions of the oligomerization zone are as follows: pressure 5.5 MPa, temperature 220° C., SV=1 h$^{-1}$. The catalyst used is a type MFI zeolite with an Si/Al ratio of 48. It is used in the form of spheres with average diameter of 2 mm. The oligomers produced, which mainly contain C8 olefinic oligomers, and C12 in smaller quantities, are fed to the cracking zone, which has the following operating conditions:

pressure: 0.2 MPa,
temperature: 520° C.,
SV=10 h$^{-1}$.

The catalyst used contains 30 wt. % of zeolite ZSM-5, dispersed in a silica-alumina matrix. It is used in the form of spheres with average diameter of 2 mm.

The cracking yields of the oligomers are shown in Table 2.

The C4/C5 fraction from cracking (apart from isobutene) is then recycled, as already mentioned.

Calculation of the overall propylene yield, taking into account the coke balance (approximately 2% in the cracking stage), gives a yield of 48% relative to the olefins in the initial charge. It might be possible to increase this yield slightly by recycling the unconverted C4/C5 olefins leaving oligomerization.

As a variant, if it is desirable to carry out combined production of propylene and gasoline (and optionally of kerosene), it is possible to increase the flow rate in the oligomerization section (without altering the cracking) and extract an additional cut of oligomers constituting a base of gasoline and optionally of kerosene.

TABLE 1

| wt. % | Oligo inlet | Oligo outlet |
| --- | --- | --- |
| C4/C5 paraffins | 11.99 | 15.65 |
| Isobutene | 0.0 | 0.0 |
| C4/C5 olefins (except isobutene) | 88.01 | 0.83 |
| Oligomers | 0.0 | 83.52 |
| Total | 100.0 | 100.0 |

TABLE 2

| wt. % | Cracking outlet |
| --- | --- |
| H2 | 0.41 |
| CH4 | 1.22 |
| C2H4 | 4.59 |
| C2H6 | 2.24 |
| C3H6 | 40.79 |
| C3H8 | 3.57 |
| C4/C5 paraffins | 6.01 |
| Isobutene | 11.83 |
| C4/C5 olefins except isobutene | 25.26 |
| Gasoline | 4.08 |
| Total | 100.0 |

EXAMPLE 2

Oligomerization of Various Olefinic Charges

Two C4 and C5 olefinic cuts are available (which may for example come from an FCC), for which a preliminary oligomerization is carried out: either of the C4 cut alone, or of the C4 cut mixed with the C5 cut (co-oligomerization). The effluents from these oligomerizations will be used in Examples 3 and 4 below.

The conditions of oligomerization are identical to those in Example 1.

The composition of the charges and of the effluents from oligomerization is shown in Table 3:

TABLE 3

| Charge or Effluent from oligomerization kg/h | C4 cut (charge) | C5 cut (charge) | Effluent from oligomerization of the C4 cut | Effluent from oligomerization of the (C4 + C5) cut |
| --- | --- | --- | --- | --- |
| C4 paraffins | 7649 | 0 | 7871 | 7871 |
| Isobutene | 125 | 0 | 6 | 6 |
| Butene-1 | 2025 | 0 | 103 | 106 |
| Butene-2 | 5069 | 0 | 254 | 324 |
| C5 paraffins | 0 | 7598 | 0 | 7844 |
| C5 olefins | 0 | 9838 | 0 | 2103 |
| C6$^+$ cut (1) | 0 | 0 | 6633 | 14048 |
| Total | 14867 | 17435 | 14867 | 32302 |

(1) A Cn$^+$ cut comprises, by definition, the cuts having at least n carbon atoms.

EXAMPLE 3

According to the Invention

The C5$^+$ cut obtained from oligomerization (co-oligomerization) of the (C4+C5) cut according to Example 2 (last column of Table 3) is cracked catalytically in the same conditions as in Example 1. The cracking yields, expressed as in the case in Example 1, as wt. % relative to the olefinic cut of the C4+C5 charge, except isobutene, are shown in Table 4:

TABLE 4

| Yields, wt. % | Cracking outlet |
| --- | --- |
| H$_2$ | 0.39 |
| CH4 | 1.15 |
| C2H4 | 5.20 |
| C2H6 | 2.44 |
| C3H6 | 28.73 |
| C3H8 | 3.35 |
| C4/C5 paraffins | 5.65 |
| Isobutene | 11.11 |
| C4/C5 olefins except isobutene | 37.40 |
| Gasoline | 4.60 |
| Total | 100.0 |

If the cracking reactor, for example in an FCC unit or a fixed-bed or moving-bed unit, or the cracked gas compressor, or the gas treatment unit are of limited capacity, it is possible to use the C6$^+$ cut obtained from oligomerization, rather than the C5$^+$ cut obtained from oligomerization, as the feed for cracking, to reduce the flow rate of cracked oligomers, with a relatively small loss of propylene.

If the charge of oligomers sent to cracking is to be reduced further, only the C8$^+$ or even C9$^+$ fraction need be sent for cracking. These different variants can also be used in the case when oligomerization is carried out in 2 Stages b1) and b3). It is possible for example to carry out a first oligomerization b1) of a C4/C5 cut, evacuate the C8+ oligomers to a fractionation zone for preparation of bases of gasoline and/or of kerosene, feed the residual C4/C5 fraction to a second oligomerization b3), then separate the second C8+ or C9+ oligomers which are used as feed for cracking.

EXAMPLE 4

Comparative

The initial C5 cut (i.e. without prior oligomerization), to which the C5+ fraction contained in the effluents from oligomerization of the C4 cut according to Example 2 has been added, is cracked catalytically in the conditions of Example 1. In this comparative example only the C4 cut is oligomerized (typically for the purposes of removing the butanes after this oligomerization and before cracking). The C5 cut, which has a relatively lower content of paraffins than the C4 cut, is cracked directly, mixed with the C5+ oligomers obtained by oligomerization of the C4 cut. The cracking yields are given in the following table:

TABLE 5

| Yields, kg/h | Cracking outlet |
| --- | --- |
| H2 | 0.24 |
| CH4 | 0.73 |
| C2H4 | 4.87 |
| C2H6 | 2.13 |
| C3H6 | 18.17 |
| C3H8 | 2.12 |
| C4/C5 paraffins | 3.57 |
| Isobutene | 7.03 |
| C4/C5 olefins except isobutene | 59.03 |
| Gasoline | 2.11 |
| Total | 100.00 |

It can be seen that the propylene yield in this comparative example is far lower than that of Example 3 according to the invention. This shows the benefit of co-oligomerizing complex cuts comprising olefins having different numbers of carbon atoms, before cracking is carried out, namely for improving the selectivity for propylene and the single-pass conversion (Note: Examples 3 and 4 cannot be compared with Example 1 because, as well as the different charge, they correspond to single-pass cracking, without recycling of the olefins that re-formed during cracking).

The process according to the invention therefore makes it possible, according to different variants, to improve the production of propylene for a given charge. It also makes it possible to reduce recycling as there is higher conversion per pass, and typically to improve the selectivity of cracking towards propylene. It can also permit the co-production of gasoline with a high octane number (in particular of gasoline rich in di-isobutene) and of propylene, or of di-isobutene (mixture of the two isomers) and of propylene, or of bases of gasoline and/or of kerosene and/or of gasoil, and of propylene.

The invention claimed is:

1. A process for the catalytic conversion of a hydrocarbon charge comprising olefins, said process comprising the following sequence of stages:
at least one Stage b) or b1) or b3) of oligomerization in which a catalytic oligomerization of said olefins is carried out in at least one reactor to obtain oligomers, said hydrocarbon charge comprising by weight at least 70% of C4+C5+C6 olefins, at least 10% of $C_4$ olefins and at least 10% of $C_5$ olefins, with a ratio $R_2$ of $C_5$ olefins to $C_4$ olefins higher than 0.5 and less than 2, and a ratio of $R_3$ of($C_4$+$C_5$ olefins) to $C_6$ olefins of greater than 10,
a Stage d) catalytic cracking of a oligomerizate charge containing a proportion of at least said oligomers is carried out in a reactor different from the oligomerization reactor, to produce propylene.

2. A process for the catalytic conversion of a hydrocarbon charge comprising olefins according to claim 1, comprising isobutene, said process comprising the following sequence of stages:
at least one Stage b) or b1) or b3) of oligomerization in which a catalytic oligomerization of the olefins contained in the charge is carried out in at least one reactor, then,
a Stage b2) or c) of fractionation in which a proportion at least of the oligomers produced is separated, and is evacuated directly without feeding the subsequent Stage d), said evacuated proportion comprising di-isobutene and/or tri-isobutene,
a Stage d) in which catalytic cracking of a proportion at least of the oligomers produced is carried out in a reactor different from the oligomerization reactor, to produce propylene.

3. A process according to claim 2, in which the following are carried out upstream of Stage d):
a first stage of limited oligomerization b1),
a Stage b2) of fractionation of the effluents of Stage b1), to produce at least one cut which is evacuated directly without feeding to subsequent Stages b3), d), said evacuated cut comprising di-isobutene and/or tri-isobutene,
a Stage b3) of final oligomerization of the effluent of Stage b2) or at least of C4 and/or C5 olefinic fractions contained in said effluent, after evacuation of the aforementioned cut comprising di-isobutene and/or tri-isobutene, and cracking the resultant final oligomerizate in Stage (d).

4. A process according to claim 3, in which the following are carried out:
Stage b1) with a charge essentially consisting of a C4 cut alone,
Stage b3), adding a C5 or C2+C5 cut to the butenes that were not converted in b1).

5. A process according to claim 1, in which the hydrocarbon charge to the oligomerization reactor comprises from 0.5 to 15 wt. % of ethylene.

6. A process according to claim 1, in which the hydrocarbon charge to the oligomerization reactor comprises from 0.5 to 15 wt. % of ethylene relative to the total of the C4,C5 and C6 olefins.

7. A process according to claim 1, in which the hydrocarbon charge to the oligomerization reactor comprises diolefinic and/or acetylenic compounds, and in which said hydrocarbon charge is first subjected to a Stage a) of selective hydrogenation for practically eliminating said diolefinic and/or acetylenic compounds.

8. A process according to claim 1, in which the catalyst used for the oligomerization stage comprises an acidic solid possessing shape selectivity, said catalyst comprising at least one zeolite, said zeolite comprising silicon and at least one element chosen from the group formed by aluminium, iron, gallium, phosphorus, boron, and aluminium, the zeolite exhibiting shape selectivity used being from the group comprising the zeolites of one of the following structural types: MEL, MFI, NES, EUO, FER, CHA, MFS, MWW, or from the group of the following zeolites: NU-85,NU-86, NU-88 and IM-5.

9. A process according to claim 1, in which the catalyst of Stage d) of catalytic cracking comprises a zeolite, cracking being carried out at a temperature comprised between 450° C. and 650° C., and a pressure comprised between 0.1 and 0.5 MPa.

10. A process according to claim 1, in which the catalyst used for the cracking stage comprises a zeolite exhibiting shape selectivity of structural type MFI, alone or mixed with another zeolite exhibiting shape selectivity chosen from the group comprising the zeolites of one of the following structural types: MEL (for example ZSM-11), NES, EUO, FER, CHA (for example SAPO-34), MFS, MWW, or the group of the following zeolites: NU-85,NU-86, NU-88 and IM-5,and in which the zeolite or zeolites used exhibiting shape selectivity have an Si/Al ratio greater than 12.

11. A process according to claim 1, in which the catalyst used for the cracking stage comprises one or more zeolites exhibiting shape selectivity, the proportion of zeolite(s) exhibiting shape selectivity being comprised between 70 and 100 wt. % relative to the total quantity of zeolite(s).

12. A process according to claim 8, in which the catalyst used in the cracking stage comprises a zeolite exhibiting shape selectivity with Si/Al ratio different from the zeolite or zeolites exhibiting shape selectivity contained in the catalyst used in the oligomerization stage.

13. A process according to claim 1, in which the catalytic cracking reactor is a fixed-bed or moving-bed or fluidized-bed reactor.

14. A process according to claim 1, wherein the ratio $R_2$ is greater than 0.7 and less than 1.5.

15. A process according to claim 1, wherein the oligomerizate charge to the cracking stage contains 20-100% by weight of olefins with at least 8 carbon atoms, and includes C9 co-dimers.

16. A process according to claim 1, wherein the oligomerizate charge to the cracking stage contains 30-100% by weight of olefins with at least 8 carbon atoms, and includes C9 co-dimers.

17. A process according to claim 1, wherein the oligomerizate charge to the cracking stage contains 50-100% by weight of olefins with at least 8 carbon atoms, and includes C9 co-dimers.

18. A process according to claim 1, wherein the oligomerizate charge to the cracking stage contains 60-100% by weight of olefins with at least 8 carbon atoms, and includes C9 co-dimers.

* * * * *

UNITED STATES PATENT AND TRADEMARK OFFICE
CERTIFICATE OF CORRECTION

PATENT NO. : 7,262,332 B2
APPLICATION NO. : 10/507853
DATED : August 28, 2007
INVENTOR(S) : Jean-Luc Duplan It is certified that error appears in the above-identified patent and that said Letters Patent is hereby corrected as shown below:

On Title Page, Item (75) Inventors: "Lyons" should read -- Lyon --
On Title Page, Item (86) PCT Date reads "May 10, 2005" should read -- September 15, 2004 --

Signed and Sealed this

Eighth Day of April, 2008

JON W. DUDAS
*Director of the United States Patent and Trademark Office*